United States Patent
Van Horn (10) Patent No.: US 6,243,599 B1
(45) Date of Patent: Jun. 5, 2001

(54) METHODS, SYSTEMS AND COMPUTER PROGRAM PRODUCTS FOR PHOTOGRAMMETRIC SENSOR POSITION ESTIMATION

(75) Inventor: Mark Harold Van Horn, Raleigh, NC (US)

(73) Assignee: MedAcoustics, Inc., Raleigh, NC (US)

(*) Notice: Subject to any disclaimer, the term of this patent is extended or adjusted under 35 U.S.C. 154(b) by 0 days.

(21) Appl. No.: 09/293,199

(22) Filed: Apr. 16, 1999

Related U.S. Application Data (63) Continuation of application No. 09/188,510, filed on Nov. 9, 1998.

(30) Foreign Application Priority Data

Nov. 10, 1997 (WO) .................................. PCT/US97/20186

(51) Int. Cl.⁷ ...................................................... A61B 5/05
(52) U.S. Cl. .............................................................. 600/407
(58) Field of Search ..................................... 600/407, 420, 600/433, 434, 435, 462, 466, 467, 528, 424, 589; 367/25, 33

(56) References Cited

U.S. PATENT DOCUMENTS

| | | |
|---|---|---|
| Re. 32,180 | 6/1986 | Chase . |
| 3,442,264 | 5/1969 | Levitt .................................. 128/2.06 |
| 3,573,394 | 4/1971 | Birnbaum ........................... 128/2.05 |
| 3,799,147 | 3/1974 | Adolph et al. ........................ 128/2.05 |
| 3,903,733 | 9/1975 | Murayama et al. ................... 73/71.4 |
| 4,008,408 | 2/1977 | Kodama ................................ 310/9.1 |
| 4,054,808 | 10/1977 | Tanaka ................................ 310/323 |
| 4,094,308 | 6/1978 | Cormier .......................... 128/2.05 R |
| 4,146,955 | 4/1979 | Young, Jr. et al. ..................... 29/594 |

(List continued on next page.)

FOREIGN PATENT DOCUMENTS

| | | |
|---|---|---|
| 32 34 584 | 3/1984 | (DE) . |
| 3531399A1 | 3/1986 | (DE) . |
| 0194823A2 | 9/1986 | (EP) . |
| 0 201 421 | 12/1986 | (EP) . |
| 0325805A1 | 8/1989 | (EP) . |
| 0 528 279 | 2/1993 | (EP) . |
| 2 507 424 | 12/1982 | (FR) . |
| 2188732 | 7/1987 | (GB) . |
| WO/90-08506 | 8/1990 | (WO) . |
| WO 93/22970 | 11/1993 | (WO) . |
| WO 94 05207 | 3/1994 | (WO) . |
| WO 95/06525 | 9/1995 | (WO) . |

OTHER PUBLICATIONS

Rosenfeld, Azriel, et al., *Segmentation*, 2d., vol. 2, Ch. 10, pp. 55–190 (Academic Press, Inc., 1982).

*Primary Examiner*—George Manuel
(74) *Attorney, Agent, or Firm*—Myers Bigel Sibley & Sajovec, P.A.

(57) ABSTRACT

Methods, systems and computer program products are provided for determining an obscured contact point based on a visible portion of an acoustic sensor of a medical device contacting a patient by acquiring a first image containing an upper surface of the acoustic sensor from a first viewpoint and a second image containing the upper surface of the acoustic sensor from a second viewpoint different from the first viewpoint. The acoustic sensor is located in the first image and the second image and the centroid of the acoustic sensor is determined based on the location of the acoustic sensor in the first image and the corresponding location of the acoustic sensor in the second image. A plane of the visible portion of the acoustic sensor is also determined based on the position of the upper surface of the acoustic sensor in the first image and the corresponding position of the upper surface of the acoustic sensor in the second image. The contact point of the obscured portion of the acoustic sensor may then be determined by projecting a predetermined depth through the centroid of the acoustic sensor in a direction having a predefined relationship with the plane of the visible portion of the acoustic sensor.

45 Claims, 5 Drawing Sheets

U.S. PATENT DOCUMENTS

| | | | |
|---|---|---|---|
| 4,226,248 | 10/1980 | Manoli | 128/773 |
| 4,234,813 | 11/1980 | Iguchi et al. | 310/366 |
| 4,255,791 | 3/1981 | Martin | 364/514 |
| 4,268,912 | 5/1981 | Congdon | 367/163 |
| 4,308,870 | 1/1982 | Arkans | 128/640 |
| 4,376,302 | 3/1983 | Miller | 367/157 |
| 4,385,255 | 5/1983 | Yamaguchi et al. | 310/335 |
| 4,387,378 | 6/1983 | Henderson | 343/854 |
| 4,406,967 | 9/1983 | Obara et al. | 310/366 |
| 4,413,630 | 11/1983 | Anderson et al. | 128/661 |
| 4,424,465 | 1/1984 | Ohigashi et al. | 310/335 |
| 4,428,380 | 1/1984 | Wong et al. | 128/715 |
| 4,458,693 | 7/1984 | Badzinski et al. | 128/715 |
| 4,491,051 | 1/1985 | Barcus | 84/1.16 |
| 4,509,227 | 4/1985 | Fraden | 128/671 |
| 4,546,777 | 10/1985 | Groch et al. | 128/715 |
| 4,549,551 | 10/1985 | Dyck et al. | 128/689 |
| 4,586,514 | 5/1986 | Schlager et al. | |
| 4,628,321 | 12/1986 | Martin | 342/379 |
| 4,630,203 | 12/1986 | Szirtes | 364/414 |
| 4,656,385 | 4/1987 | Tanaka | 310/348 |
| 4,697,597 | 10/1987 | Sanz et al. | 128/699 |
| 4,700,712 | 10/1987 | Schmid | 128/699 |
| 4,712,565 | 12/1987 | Katz et al. | 128/715 |
| 4,742,458 | 5/1988 | Nathans et al. | 364/417 |
| 4,777,961 | 10/1988 | Saltzman | 128/715 |
| 4,781,200 | 11/1988 | Baker | 128/670 |
| 4,784,154 | 11/1988 | Shirley et al. | 128/715 |
| 4,792,145 | 12/1988 | Eisenberg et al. | 128/715 |
| 4,803,986 | 2/1989 | Dufresne et al. | 128/385 |
| 4,803,996 | 2/1989 | Peel et al. | 128/710 |
| 4,805,633 | 2/1989 | Kotani et al. | 128/715 |
| 4,812,976 | 3/1989 | Lundy | 364/413.06 |
| 4,821,584 | 4/1989 | Lembke | 73/862.68 |
| 4,840,183 | 6/1989 | Takahashi et al. | 128/715 |
| 4,842,411 | 6/1989 | Wood | 356/376 |
| 4,862,144 | 8/1989 | Tao | 340/573 |
| 4,862,361 | 8/1989 | Gordon et al. | 364/413.06 |
| 4,862,897 | 9/1989 | Eisenberg et al. | 128/715 |
| 4,905,706 | 3/1990 | Duff et al. | 128/701 |
| 4,924,875 | 5/1990 | Chamoun | 128/696 |
| 4,928,705 | 5/1990 | Sekhar et al. | 128/773 |
| 4,947,859 | 8/1990 | Brewer et al. | 128/715 |
| 4,957,369 | 9/1990 | Antonsson | 356/376 |
| 4,967,760 | 11/1990 | Bennett, Jr. et al. | 128/715 |
| 4,991,581 | 2/1991 | Andries | 128/715 |
| 5,002,058 | 3/1991 | Martinelli | 128/662 |
| 5,002,060 | 3/1991 | Nedivi | 128/671 |
| 5,003,605 | 3/1991 | Phillipps et al. | 381/67 |
| 5,010,889 | 4/1991 | Bredesen et al. | 128/715 |
| 5,012,815 | 5/1991 | Bennett, Jr. et al. | 128/715 |
| 5,025,809 | 6/1991 | Johnson et al. | 128/715 |
| 5,035,247 | 7/1991 | Heimann | 128/715 |
| 5,036,857 | 8/1991 | Semmlow et al. | 128/715 |
| 5,086,776 | 2/1992 | Fowler, Jr. et al. | 128/661.09 |
| 5,109,863 | 5/1992 | Semmlow et al. | 128/715 |
| 5,129,403 | 7/1992 | Henriquez et al. | 128/773 |
| 5,140,992 | 8/1992 | Zuckerwar et al. | 128/715 |
| 5,164,627 | 11/1992 | Popek | 310/313 B |
| 5,176,153 | 1/1993 | Eberhardt | 128/897 |
| 5,213,108 | 5/1993 | Bredesen et al. | 128/715 |
| 5,218,969 | 6/1993 | Bredesen et al. | 128/710 |
| 5,301,679 | 4/1994 | Taylor | 128/773 |
| 5,315,512 | 5/1994 | Roth | 364/413.25 |
| 5,337,752 | 8/1994 | Reeves | 128/700 |
| 5,363,401 | 11/1994 | Lucas et al. | 375/1 |
| 5,365,937 | 11/1994 | Reeves et al. | 128/715 |
| 5,381,804 | 1/1995 | Shambroom | 128/731 |
| 5,455,385 | 10/1995 | Newton et al. | 174/52.4 |
| 5,501,229 | 3/1996 | Selker et al. | 128/696 |
| 5,553,113 | 9/1996 | Weedon | 378/98.5 |
| 5,595,188 | 1/1997 | Kassal | 128/773 |
| 5,598,845 | 2/1997 | Chandraratna et al. | 128/662.03 |
| 5,617,869 | 4/1997 | Austin et al. | 128/691 |
| 5,638,823 | 6/1997 | Akay et al. | 128/691 |
| 5,645,065 | * 7/1997 | Shapiro et al. | 600/424 |
| 5,673,702 | 10/1997 | Albrecht et al. | 128/712 |
| 5,680,513 | 10/1997 | Hyland et al. | 395/21 |
| 5,686,917 | 11/1997 | Odom et al. | 341/141 |
| 5,687,738 | 11/1997 | Shapiro et al. | 128/715 |
| 5,704,365 | 1/1998 | Albrecht et al. | 128/702 |
| 5,718,233 | 2/1998 | Selker et al. | 128/696 |
| 5,724,967 | 3/1998 | Venkatachalam | 128/633 |
| 5,724,968 | 3/1998 | Iliff | 128/630 |
| 5,724,983 | 3/1998 | Selker et al. | 128/696 |
| 5,755,571 | * 5/1998 | Companion | 600/589 |
| 5,796,920 | 8/1998 | Hyland | 395/22 |
| 5,807,268 | 9/1998 | Reeves et al. | 600/528 |
| 5,885,222 | 3/1999 | Kassal et al. | 600/528 |
| 6,088,294 | * 7/2000 | Leggett, III et al. | 367/25 |

OTHER PUBLICATIONS

Rosenfeld, Azriel, et al., *Description*, 2d., vol. 2, Ch. 12, pp. 276–346 (Academic Press, Inc., 1982).

Horn, "Computing Depth," Robot Vision, Ch. 13.6, pp. 311–312 (MIT Press 1986).

Nilsson et al., "A Combined Microphone for Simultaneous Recording of Pulse, Phono and Reference ECG," Electromedica, vol. 2, No. 76, pp. 64–68 (1976).

Oestreicher, "Field and Impedance of an Oscillating Sphere in a Viscoelastic Medium with an Application to Biophysics," J. Acoust. Soc. Am., vol. 23, No. 6, pp. 707–714 (Nov. 1951).

Verburg, "Transmission of Vibrations of the Heart to the Chestwall," Adv. Cardiovasc. Phys., vol. 5, (Part III), pp. 84–103 (1983).

*Gabor Spectrogram*, DSP Software Development, National Instruments, Austin, TX (believed to be prior art).

Akay et al., Application of Adaptive FTF/FAEST Zero Tracking Filters to Noninvasive Characterization of the Sound Pattern Caused by Coronary Artery Stenois Before and After Angioplasty, *Annals of Biomedical Engineering*, vol. 21, pp. 9–17 (1993).

Akay et al., Application of Adaptive Filters to Noninvasive Acoustical Detection of Coronary Occlusions Before and After Angioplasty, *IEEE Transactions on Biomedical Engineering*, vol. 39, No. 2, pp. 176–183 (Feb. 1992).

Akay et al., Noninvasive acoustical detection of coronary artery disease using the adaptive line enhancer method, *Medical & Biological Engineerig & Computing*, vol. 30, pp. 147–154 (Mar. 1992).

Akay et al., Noninvasive Acoustical Detection of Coronary Artery Disease: A Comparataive Study of Signal Processing Methods, *IEEE Transactions on Biomedical Engineering*, vol. 40, No. 6, pp. 571–5784 (Jun. 1993).

Donnerstein, Continuous Spectral Analysis of Heart Murmurs for Evaluating Stenotic Cardiac Lesions, *The Am. Journ. Card.*, vol. 64, pp. 625–630 (Sep. 15, 1989).

Durand et al., Evaluation of FFT–Based and Modern Parametric Methods for the Spectral Analysis of Bioprosthetic Valve Sounds, *IEEE Trans. on Biomedical Eng.*, vol. BME–33, No. 6, pp. 572–578 (Jun. 1986).

Foale et al., Detection of aortic porcine valve dysfunction by maximum entrophy spectral analysis, Circulation, vol. 68, No. 1, pp. 42–49 (Jul. 1983).

Fraden, Application of Piezo/Pyroelectric Films in Medical Transducers, *Jour. of Clinical Eng.*, vol. 13, No. 3, pp. 133–138 (Mar.–Apr. 1988).

Haralick, R. et al., *Computer and Robot Vision*, Addison-Wesley Publ. Co., NY, NY, pp. 31–40 (believed to be prior art).

Iwata et al., Algorithm for Detecting the First and Second Heart Sound by Spectral Tracking, *Medical & Biological Engineering and Computing*, pp. 19–26 (Jan. 1980).

Johnson et al., Estimation of the Severity of Aortic Valve Stenosis by Frequency Analysis of the Murmur, *J. Am. Coll. Cardiol.*, 1(5):1315–23 (1983).

Johnson et al., Evaluation of Aortic Stenosis by Spectral Analysis of the Murmur, *JACC*, vol. 6, No. 1, pp. 55–65 (Jul. 1985).

Joo et al., Pole–Zero Modeling and Classification of Phonocardiograms, *IEEE Trans. on Biomedical Eng.*, vol. BME–30, No. 2, pp. 110–118 (Feb. 1983).

Kagawa et al., Real–time sound spectroanalysis for diagnosis of malfunctioning prosthetic valves, *J. Thorac. Cardiovasc. Surg.*, vol. 79, pp. 671–679 (May 1980).

Lees et al. Phonoangiography: A New Noninvasive Diagnostic Method for Studying Arterial Disease, *Proceedings of the National Academy of Sciences*, No. 67, No. 2, pp. 935–942 (Oct. 1970).

Qian et al., Orthogonal–Like Discrete Gabor Expansion, *26th Conf. on Infor. Sci. an Systems*, Princeton University (Mar. 18, 1992).

Semmlow et al., Noninvasive Detection of Coronary Artery Disease Using Parametric Spectral Analysis Methods, *IEEE Engineering in Medicine and Biology Magazine*, pp. 33–36 (Mar. 1990).

Semmlow et al, Coronary Artery Disease—Correlates Between Diastolic Auditory Characteristics and Coronary Artery Stenoses, *IEEE Transactions on Biomedical Engineering*, vol. BME–30, No. 2, pp. 136–139 (Feb. 1983).

Semmlow et al, Non–Invasive Diagnosis of Coronary Artery Disease by Enhanced Coronary Phonocardiography, *IEEE Frontiers of Eng. in Health Care*, pp. 181–185 (1982).

Stein et al., Frequency Spectra of the First Heart Sound and of the Aortic Component of the Second Heart Sound in Patients with Degenerated Porcine Bioprosthetic Valves, *The Am. Journ. of Carad.*, vol. 53, pp. 557–581 (Feb. 1, 1984).

von Glerke, H. et al., Physics of Vibrations in Living Tissues, *J. App. Physiology*, vol. 4, pp. 886–900 (Jun. 1952).

Wang et al., Modeling Sound Generation in Stenosed Coronary Arteries, *IEEE Transactions on Biomedical Engineering*, vol. 37, No. 11, pp. 1087–1094 (Nov. 1990).

Xu, Gang, et al., Reconstruction Techniques, *Epipolar Geometry in Stereo, Motion and Object Recognition—A Unified Approach*, Ch. 3.4.3, pp, 153–155.

Faugera, Olivier, Ordering, *Three–Dimensional Computer Vision—A Geometric Viewpoint*, Ch. 6, pp. 178–181 (MIT Press, 1993).

Haralick, Robert M., et al ., Structure from Stereo by Using Correspondence, *Computer and Robot Vision*, vol. II, Ch. 16.6 (Addison–Wesley 1993).

Longuet–Higgins, H.C., A computer algorithm for reconstructing a scene from two projections, *Nature*, vol. 293, pp. 133–135 (Sep. 10, 1981).

Horn, Berthold, Disparity between the Two Images, *Robot Vision*, Ch. 13.1, pp. 300–301, 320–322 (MIT Press 1986).

* cited by examiner

METHODS, SYSTEMS AND COMPUTER PROGRAM PRODUCTS FOR PHOTOGRAMMETRIC SENSOR POSITION ESTIMATION

RELATED APPLICATIONS

The present application is a continuation-in-part of commonly assigned U.S. patent application Ser. No. 09/188,510 entitled "NON-INVASIVE TURBULENT BLOOD FLOW IMAGING SYSTEM" filed Nov. 9, 1998, the disclosure of which is incorporated by reference herein as if set forth fully.

FIELD OF THE INVENTION

The present invention relates to the measurement of acoustic signals in a patient and more particularly, to the determination of the location of acoustic sensors in an array on a patient.

BACKGROUND OF THE INVENTION

Acoustic signals generated by turbulent blood flow may be utilized for the non-invasive detection of stenosis. To detect acoustic signals generated by turbulent blood flow, an array of sensors are placed on a patient's chest. Typically, these sensors have been configured in a fixed array such that the spatial relationship between the sensors was known. However, because patients differ in physical characteristics, it may be advantageous to use discrete sensors which may be positioned on a patient in an optimal "acoustic window" for monitoring blood flow.

One problem which may arise in a system where discrete sensors are utilized to detect acoustic signals relates to the determination of the spatial relationship of the sensors. In order to utilize advanced beam forming techniques on the received signals at the sensors, it is preferred that the spatial relationship of the sensors be accurately determined. One technique which may be utilized to determine the locations of the sensors involves an articulating arm which is calibrated and used to make physical measurements of the sensor locations by placing the tip of the articulating arm at each of the sensor locations. However, the use of an articulating arm may be slow and the contact between the arm and the patient or the sensor may move the sensor and unfortunately, thereby, provide an inaccurate reading. Furthermore, if the locations of the sensors are dynamically determined, by whatever technique, such a determination may still not provide a sufficiently accurate spatial relationship of the sensors as it is the point of contact between the sensors and the patient which are utilized in beam forming. These contact points are obscured once the sensors are placed on the patient and, therefore, may be difficult, if not impossible, to directly measure.

In light of the above discussion, a need exists for improvements in the determination of the spatial relationship between sensors placed on a patient.

SUMMARY OF THE INVENTION

In light of the above discussion, it is an object of the present invention to provide for the determination of the spatial relationship of the contact points of sensors in an array without disturbing the sensors.

A further object of the present invention is to provide for the determination of the spatial relationship of the contact point of sensors in an array without requiring a fixed relationship between the sensors.

Still another object of the present invention is to provide for the determination of the spatial relationship of the contact point of sensors in an array even when the contact points of the sensors are obscured.

These and other objects of the present invention are provided by methods, systems and computer program products which determine an obscured contact point based on a visible portion of an acoustic sensor of a medical device contacting a patient by acquiring a first image containing an upper surface of the acoustic sensor from a first viewpoint and a second image containing the upper surface of the acoustic sensor from a second viewpoint different from the first viewpoint. The location of the centroid of the acoustic sensor is determined in three dimensional space. The centroid may be determined in three dimensional space by determining the centroid of the acoustic sensor in each image and then determining the location in three dimensional space from the locations in the images. A plane of the visible portion of the acoustic sensor is also determined based on the position of the upper surface of the acoustic sensor in the first image and the corresponding position of the upper surface of the acoustic sensor in the second image. The contact point of the obscured portion of the acoustic sensor may then be determined by projecting a predetermined depth through the centroid of the acoustic sensor in a direction having a predefined relationship with the plane of the visible portion of the acoustic sensor.

Because the contact point can be determined based on the image data, the sensor need not come into physical contact with any measuring devices which may cause the position of the sensor to change during measurement. Accordingly, the present invention provides for the determination of the position of the contact point of a sensor without physically disturbing the sensor. The location of a sensor may be determined using images taken each time the sensor is applied to a patient. Also, by determining the centroid of the sensor in a plane corresponding to the upper surface of the sensor and then projecting normal to that plane to a depth of the sensor, the contact point may be determined even when the contact point of the sensor is obscured (i.e. when the sensor is conformally engaged to the patient's skin).

In a further embodiment of the present invention, the plane is determined by locating corners of the visible portion of the upper surface of the acoustic sensor based on the position of the acoustic sensor in the first image and the corresponding position of the uppers surface of the acoustic sensor in the second image. Lines which pass through the corners of the visible portion of the acoustic sensor are determined so that a cross product of the lines will result in a vector normal to the plane of the upper surface of the sensor. The contact point may then be determined by projecting the predetermined depth through the centroid of the upper surface in the direction of the cross product.

In a still further embodiment, the corners are located through the use of calipers which are orthogonal to the edges of the sensor in the image. The locations of the corners of the visible portion of the acoustic sensor are then determined by moving the calipers until they first contact the sensor. The contact point is then utilized as a corner point.

In a preferred embodiment of the present invention, the visible portion of the acoustic sensor is a quadrangle. In such a case the selected corners for the lines for use in the cross product are alternating (opposing) corners of the quadrangle.

In a still further embodiment of the present invention, contact points of a plurality of acoustic sensors are determined. The relative spatial relationship between the plurality of acoustic sensors may then be determined based on the determination of the contact point of each of the plurality of acoustic sensors.

By determining each of the contact points of the sensors in a sensor array in three dimensional space, the relative positions of the contact points of the sensors may be determined from the respective location in space of the contact point of the each sensor. Because the contact point of each sensor may be determined individually, the determination of the spatial relationship of the contact point of each of the sensors in the sensor array does not require a fixed relationship between the sensors.

In a particular embodiment of the present invention, the first image is acquired by a first camera and the second image is acquired by a second camera. Preferably, these images are acquired simultaneously. These cameras may be charge coupled device cameras. In any event, in such a two camera embodiment, the first camera and the second camera may be calibrated so as to determine the relationship between the first viewpoint and the second viewpoint. Such calibration may be accomplished by acquiring at the first camera a first reference image containing a predefined configuration of landmarks and acquiring at the second camera a second reference image containing the predefined configuration of landmarks. The spatial relationship between an image plane of the first camera and an image plane of the second camera may then be determined based on the first and second reference images.

In a particular embodiment of the present invention, the calibration may involve computing camera parameters for each of the first and second cameras. Object-space coordinates for each camera are then estimated using corresponding points from at least two images of the same scene. Calibration of the cameras is indicated by coincidence of the object space coordinates for the corresponding points.

In still further embodiments of the present invention, the sensor has a visible surface which is a retro-reflective surface. Furthermore, an infrared illumination source may also be provided and configured so as to illuminate the sensor. The combination of the reflective surface, the infrared illumination and an infrared filter may substantially increase the contrast in the image so that the upper surface of the sensor appears brighter than the rest of the image. Thus, the detection of the sensor in the image may be more accurate or simplified. In still another embodiment of the present invention, the location of sensors in the first and second images is determined by locating sensor positions in the first image and locating sensor positions in the second image. A correspondence between the sensor positions in the first image and the sensor positions in the second image is then determined so that a sensor position in the first image is associated with the corresponding sensor position the second image. Such a correspondence may be determined by determining an epipolar line for a sensor position in the first image. It may then be determined which of the sensor positions in the second image the epipolar line intersects. A sensor position in the second image which the epipolar line intersects is then associated with the sensor position in the first image.

In a specific embodiment of the present invention, the association of positions in the first image with positions in the second image may be accomplished by determining if a plurality of sensor positions in the second image intersect the epipolar line. Sensor positions in the first image are then associated with sensor positions in the second image which intersect the epipolar line in an order in which the sensor positions in the first image intersect the epipolar line. Furthermore, whether a sensor position intersects an epipolar line may be determined by determining if the epipolar line intersects a bounding box around a sensor position. Signed distances between the epipolar line and opposite corners of the bounding box are then determined. The epipolar line intersects the sensor position if the signed distances between the epipolar line and the opposite corners of the bounding box are of opposite signs.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As will be appreciated by one of skill in the art, the present invention may be embodied as methods or devices. Accordingly, the present invention may take the form of an entirely hardware embodiment, an entirely software embodiment or an embodiment combining software and hardware aspects. In the figures, regions, shapes and layers may be exaggerated for clarity.

Figure 1:
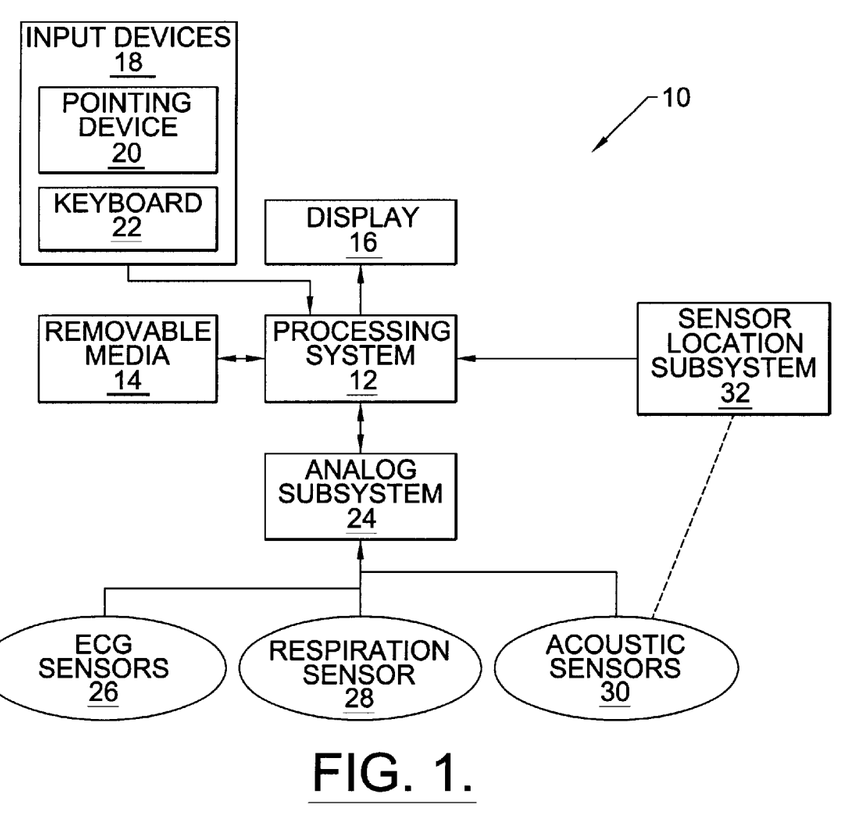
FIG. 1 is a block diagram of a system for measuring acoustic signals suitable for use with the present invention.

The present invention provides methods, systems and computer program products for determining the contact points of an array of sensors which are placed on a patient for measuring acoustic signals from acoustic sources within the patient. Such a determination may be particularly useful in such a system for detecting arterial stenosis within the patient through the non-invasive measurement of acoustic signals. The present invention, therefore, is preferably incorporated as part of a sensor location subsystem incorporated in a system for measuring acoustic signals from a patient. FIG. 1 illustrates one embodiment of a system for measuring acoustic signals suitable for use with the present invention. As seen in FIG. 1, the acoustic measuring system 10 includes a processing system 12 which preferably has associated with it a display 16, input devices 18, such as a pointing device 20 and a keyboard 22, and removable media 14 for providing data to and storing data from the processing system 12. The processing system 12 may be a personal computer, workstation, mainframe or other general purpose processing system. Similarly, processing system 12 may be a dedicated processing system such as a digital signal processor or other such dedicated processing system. Furthermore, the processing system 12 will typically utilize an operating system, such as Microsoft® Windows95®, or other such operating systems so as to control the interface with the display 16, input devices 18 and removable media 14. The operating system will also, typically, provide for execution of application programs written to execute on processing system 12. The present invention, therefore, may be implemented as an application or other such computer program which executes on the processing system 12. Furthermore, as will be appreciated by those of skill in the art, various other conventional aspects of the processing system 12 have not been illustrated in FIG. 1 but will typically be incorporated into processing system 12. For example, processing system 12 may include fixed storage, such as a hard disk, memory, cache, communications interfaces such as serial and parallel ports, modems or the like, as well as network interfaces, such as an Ethernet, Token Ring or other such network interfaces. Furthermore, processing system 12 may also include multiple types of removable storage such as a CDROM, ZIP drive, tape drive or other such removable storage media.

As is further illustrated in FIG. 1, the acoustic measuring system 10 also includes an analog subsystem 24 which provides an interface for receiving and amplifying signal from electrocardiogram (ECG) sensors 26, a respiration sensor 28 and acoustic sensors 30. The acoustic measuring system 10 utilizing the present invention also includes a sensor location subsystem 32 which provides information to the processing system 12 so as to allow for the accurate determination of the relative locations of the acoustic sensors 30.

While the details of operation of each aspect of the acoustic measurement system 10 are not essential to understanding of the present invention, in brief, the acoustic system 10 operates by placing the acoustic sensors 30, the ECG sensors 26 and the respiration sensor 28 on a patient. The processing system 12 then utilizes information from the sensor location subsystem 32 to determine the relative locations of the contact points with the patient of the acoustic sensors 30. The analog subsystem 24 receives the output of the various sensors 26, 28 and 30 and provides this information, in either analog or digital format, to the processing system 12. The processing system 12 then utilizes beamforming techniques to process the sensor information to provide information as to the presence of acoustic sources, such as turbulent blood flow, within the patient. This processing may occur in real time or the sensor information may be stored and processed at a later time or even copied to the removable storage media 14 and processed on a separate processing system. A detailed description of a system such as is described in FIG. 1 is provided in commonly assigned U.S. patent application Ser. No. 09/188,510 entitled "NON-INVASIVE TURBULENT BLOOD FLOW IMAGING SYSTEM" filed Nov. 9, 1998, the disclosure of which is incorporated by reference herein as if set forth fully.

Figure 2:
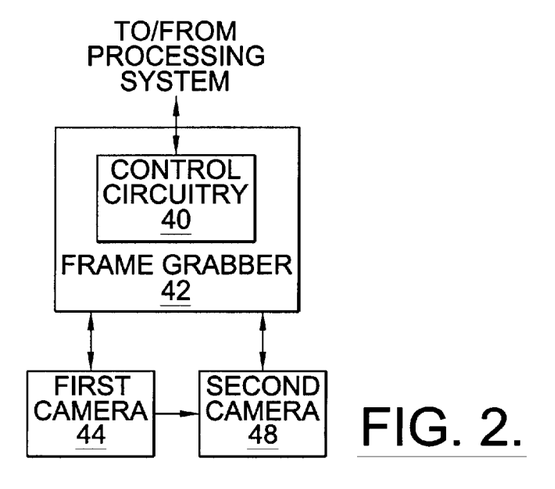
FIG. 2 is a block diagram of the Sensor Location Subsystem of FIG. 1.

A sensor location subsystem 32 according to one embodiment of the present invention will now be described with reference to FIG. 2. As seen in FIG. 2, the sensor location subsystem 32 suitable for photogrammatically determining the contact points of sensors 30 (FIG. 1) placed on a patient includes control circuitry 40 for interfacing with the processing system 12. Such control circuitry 40 provides data from frame grabber 42 to the processing system 12. As illustrated in FIG. 2, the first camera 44 and the second camera 48 are configured in a master-slave configuration such that causing the first camera 44 to acquire an image also causes the second camera 48 to acquire an image. Such a master-slave configuration of cameras to create a stereo camera are known to those of skill in the art and, therefore, will not be described further herein. Alternatively, the control circuitry 40 may also be utilized to control operation of the first camera 44 and the second camera 48 so as to control when images are obtained from the first and second cameras 44 and 48. Preferably, the first and second cameras 44 and 48 capture images simultaneously or substantially simultaneously (i.e. at a close enough period of time such that patient movement does not affect the positions of sensors as viewed by the respective cameras). The frame grabber 42 holds the captured image data in digital format, until the data may be provided to the processing system 12 through the control circuitry 40. Furthermore, the sensor location subsystem 32 may include an infra-red illumination source (not shown) for illuminating the sensors 30 so as to enhance identification of the sensors in images. Also, the cameras may include an infrared filter so as to increase contrast in acquired images.

As will be appreciated by those of skill in the art, the cameras 44 and 48, frame grabber 42 and control circuitry 40 may be incorporated as separate hardware components or may be incorporated into processing system 12. Commercially available charge coupled device (CCD) cameras and video capture systems suitable for use in the present invention include a Sony XC55-BB camera with a 12 mm focal length lens and an Integral Technologies FlashBus MV Pro frame grabber. Furthermore, the distribution of functions between the blocks in the block diagram of FIG. 2 is for illustrative purposes only such that other distributions may be utilized while still benefiting from the teachings of the present invention.

Figures 3, 4:
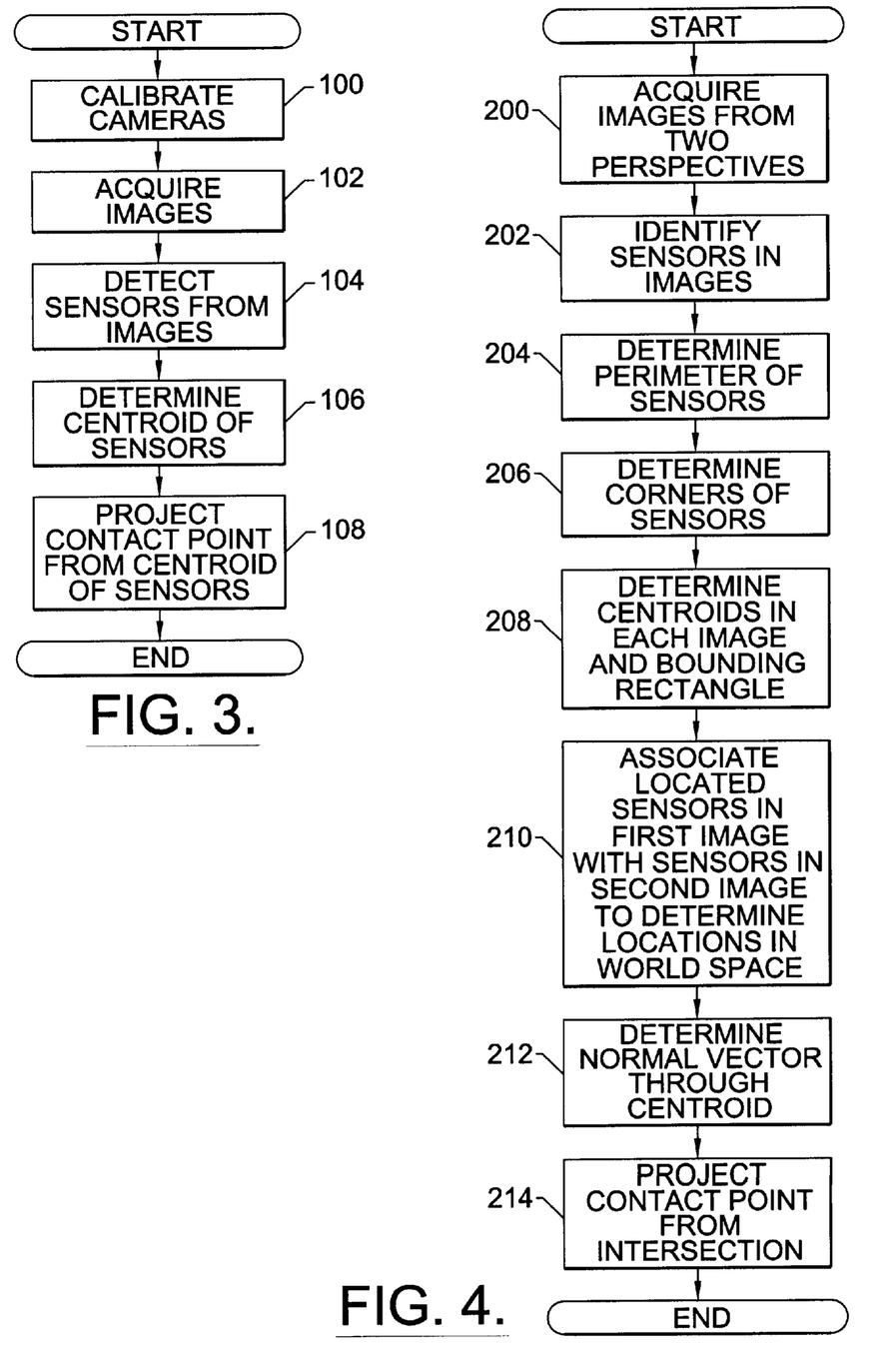
FIG. 3 is a flow chart illustrating operations according to one embodiment of the present invention.
FIG. 4 is a flow chart further illustrating operations according to one embodiment of the present invention.
Figure 5:
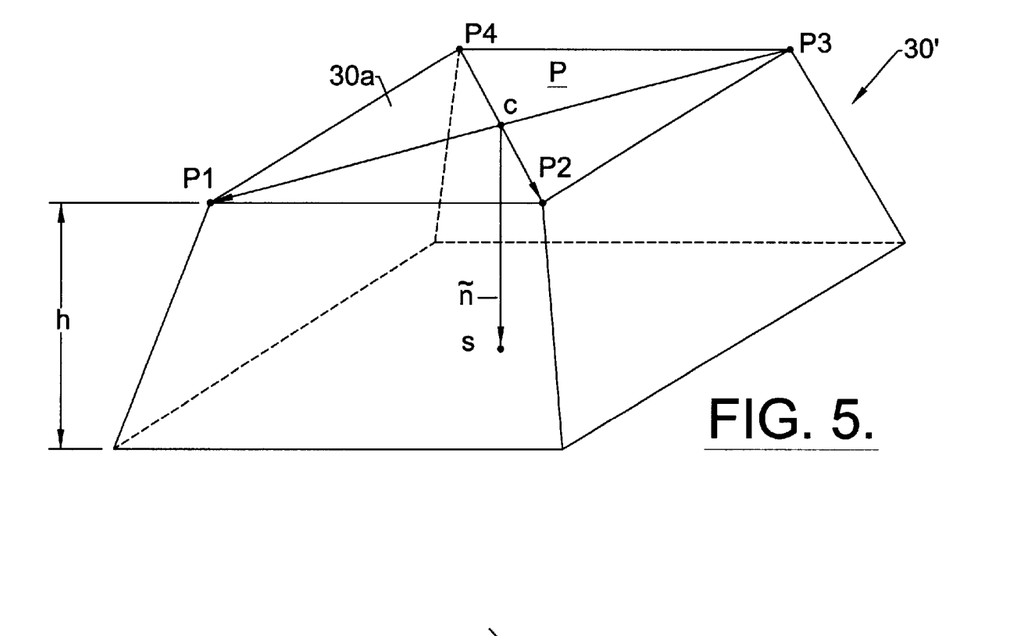
FIG. 5 is a three-dimensional schematic of one form of an acoustic sensor which has a quadrangular top.

Operation of the system of FIGS. 1 and 2 to determine the contact points of sensors 30 will now be described with respect to FIGS. 3 and 5. FIGS. 3 and 5 are flow chart illustrations. It will be understood that each block of the flowchart illustrations, and combinations of blocks in the flowchart illustrations, can be implemented by computer program instructions. These program instructions may be provided to a processor to produce a machine, such that the instructions which execute on the processor create means for implementing the functions specified in the flowchart block or blocks. The computer program instructions may be executed by a processor to cause a series of operational steps to be performed by the processor to produce a computer implemented process such that the instructions which execute on the processor provide steps for implementing the functions specified in the flowchart block or blocks.

Accordingly, blocks of the flowchart illustrations support combinations of means for performing the specified functions, combinations of steps for performing the specified functions and program instruction means for performing the specified functions. It will also be understood that each block of the flowchart illustrations, and combinations of blocks in the flowchart illustrations, can be implemented by special purpose hardware-based systems which perform the specified functions or steps, or combinations of special purpose hardware and computer instructions.

FIG. 3 provides a general overview of the operations of the acoustic measuring system 10 to determine contact points of sensors 30 utilizing the sensor location subsystem 32. As seen in FIG. 3, at block 100 an initial calibration of the cameras 44 and 48 is performed so as determine the spatial relationship between the focal planes of the two cameras. This calibration may be performed, for example, by imaging in both cameras a pattern of landmarks with a known spatial relationship. For example, a fixed array of points may be placed where the points are within both cameras field of view. Images of the fixed array may then be taken and stored by the frame grabber 42 and provided to the processing system 12 through control circuitry 40. Because the relationship between the points in the fixed array is known, the relationship of the focal planes of the cameras 44 and 48 may be derived utilizing conventional camera calibration techniques known to those of skill in the art and as described in more detail below. The calibration of the cameras 44 and 48 need only be carried out once unless focal planes of the cameras 44 and 48 are moved with respect to each other or other characteristics of the cameras 44 and 48 are altered. However, the calibration may also be carried out for each use of the acoustic measuring system 10 so as to assure that the cameras 44 and 48 have not moved.

After calibration and after placement of the sensors 30 on a patient, the cameras 44 and 48 are controlled so as to acquire images of the sensors 30 on the patient (block 102). As described above, these images are preferably acquired essentially simultaneously. The images may be stored in the frame grabber 42 and then provided to the processing system 12 through control circuitry 40. After receiving the images, the processing system 12 processes the images to detect the sensors in the images (block 104). The centroids of the detected sensors are then determined (block 106) and a linear projection from the centroid of the sensor is made perpendicular to the plane of the top surface of the sensor. The contact point is then determined to be a point along the linear projection from the centroid at the depth corresponding to the thickness of the sensor (block 108). This determination of the contact points may be made for each sensor or may be made for select sensors which act as reference points if the other sensors have a fixed spatial relationship to the reference sensors.

FIG. 4 describes in more detail the operations of blocks 102 through 108 of FIG. 3. FIG. 4 will be described with reference to FIG. 5, which is a diagram of a sensor which may be utilized with the present invention. As seen in FIG. 5, the sensor 30' has a contact point S at a depth (d) below an upper surface in a plane $\underline{P}$. While the sensor 30' of FIG. 5 is illustrated as having an upper or visible surface 30a which is a quadrangle, sensor contact points may be autonomously estimated from a stereo image pair of the upper surface of any arbitrary sensor shape as long as the centroid of the shape may be determined. However, the complexity of the centroid determination may increase as the sensor geometry becomes more complex. As used herein, the term "upper surface" refers to a surface of the sensor which is opposite the surface of the sensor in contact with the patient. Alternatively, a quadrangle, or other geometric shape, used to determine a contact point by providing an outline on a sensor top which is not quadrangular, e.g., round or polygonal. Examples of sensors which may be suitable for use with the present invention are provided in commonly assigned U.S. patent application Ser. No. 09/136,933 entitled "Thin Film Piezoelectric Polymer Sensor," in U.S. patent application Ser. No. 09/188,434, entitled "Acoustic Sensor Array for Non-invasive Detection of Coronary Artery Disease," in U.S. patent application Ser. No. 60/122,264, entitled "Low Profile Acoustic Sensor" and in U.S. Pat. No. 5,885,222, entitled "Disposable Acoustic Pad Sensors," the disclosures of which are incorporated by reference as if set forth fully herein.

To the extent that the upper surface of a sensor does not form a plane, it is preferred that the corners of the upper surface of the sensor lie in a plane which is parallel to a plane of contact of the sensor with the patient. If such is not the case, then it is preferred that the plane of the corners of the upper surface of the sensor be in a fixed relationship with the plane of contact of the sensor with the patient so that a vector having a fixed relationship with the plane of the visible corners may be determined. Furthermore, to the extent that all of the corners of the upper surface are not visible, the present invention may still be utilized as long as the shape of the upper surface of the sensor is known.

Returning to FIG. 4, as described above, the determination of sensor contact point(s) begins by acquiring a stereo image pair of the desired sensor (block 200). The sensor contact point, S, is estimated using only information derived from the stereo image pair which includes the upper surface of the sensor. Identification of the upper surface of the sensor in the stereo images may be facilitated by attaching a retro-reflective material (e.g., 3M 7610 High Gain Reflective Sheeting). The reflective material preferably covers the area bounded by points P1, P2, P3, and P4 (quadrangle corners) shown in FIG. 5. Furthermore, the identification (segmentation) of the sensor tops may be further facilitated by use of infra-red illumination and use of cameras 44 and 48 capable of imaging in the infra-red range of the spectrum.

After acquisition of the images, the sensors are located in each image via a segmentation process (block 202), such as described in Chapter 10 of Rosenfeld, A. and Kak, A. C., *Digital Picture Processing*, (1982) Second Edition, Vol. 2, New York: Academic Press, Inc. This segmentation process identifies the pixels in the digital images corresponding to each sensor based on gray-scale levels such that a threshold is determined for a gray-scale value and pixels in the images are considered as part of a sensor or not based on the relationship of the pixel gray-scale value to a threshold. Alternatively, other common characteristics could be utilized for the segmentation process, such as for example, color, intensity or the like.

Figure 6:
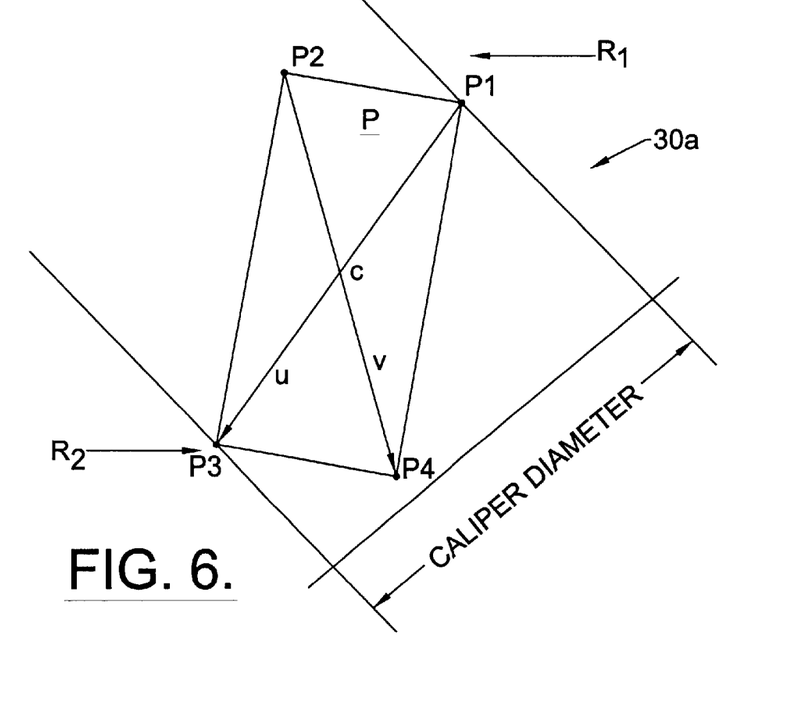
FIG. 6 depicts an image with caliper diameter and corner locations of teh quadrangular top of the FIG. 5 schematic sensor.

Centroid location and sensor top orientation data are derived for each detected sensor in the images. The centroid and sensor top orientation may be determined utilizing a connected component methodology such as is described in Rosenfeld, A. and Kak, A. C., *Digital Picture Processing*, (1982) Second Edition, Vol. 2, New York: Academic Press, Inc. The perimeter or boundary pixels of the quadrangle area are identified using a boundary following method (block 204). An appropriate boundary following algorithm is set forth in Rosenfeld, A. and Kak, A. C., *Digital Picture Processing*, (1982) Second Edition, Vol. 2, New York: Academic Press, Inc. Thereafter, corner pixels or boundary points of the actual or superimposed sensor top quadrangle are determined (block 206). In FIGS. 5 and 6, these boundary points or corners P1, P2, P3 and P4 are listed in a counter-clockwise order. The corners P1, P2, P3 and P4 which define the plane $\underline{P}$ as shown by FIGS. 5 and 6. As shown in FIG. 6, the corner points may be determined using the quadrangle orientation (from the connected component method) to define two rays $R_1$ and $R_2$ as "calipers" which are oriented positively or negatively, e.g., +30 and −30 degrees from the quadrangle's orientation. The quadrangle boundary or perimeter is projected onto these rays and the caliper or feret diameter is determined. As is seen in FIG. 6, the caliper corresponds to the distance between the intersection of rays $R_1$ and $R_2$ with alternating ones of the corners in the set of corners. Thus, the contact points between the rays of the calipers and the quadrangle may be utilized as the corners of the quadrangle. This process is repeated with two more rays as calipers which are oriented to determine the other two corner points of the quadrangle. Thus, if the first set of rays are oriented to +30 degrees from the quadrangle's orientation, the second set of rays may be oriented −30 degrees from the quadrangle's orientation.

The centroid C of the quadrangle is determined as part of the connected component methodology and is the centroid of the area of a sensor. Similarly, a bounding rectangle is also determined as part of the connected component methodology. The centroid is preferably determined in each image and then, as described below, translated to three dimensional or "object" space using the centroid from each image (block 208). Once determined, the centroid and corner pixel coordinates of the upper surface of the sensor in each image are used to compute the position of the corresponding points of the sensor in object or world space (block 210) using conventional point reconstruction methods, such as is described at pages 153 through 155 of Xu, G. and Z. Y. Zhang, *Epipolar Geometry in Stereo, Motion and Object Recognition: A Unified Approach* (1996) Kluwer Boston, Mass.: Academic Publishers.

Prior to computing point locations from the images, features from the two separate images are matched (i.e. conjugate pairs identified). Given a set of pixel coordinates and the projection matrices from two cameras, the task is to determine which pixel coordinates in a first image correspond to a set of coordinates in image a second image. One way to solve this "correspondence problem" is to compute the cross correlation between an image feature from the first image and the second image. Unfortunately, with multiple sensors within a single image, the shape of the image features are similar. Thus, cross correlation merely gives the location of the image features and may not be useful since each feature's pixel coordinates are known from the connected component analysis. Furthermore, cross correlation may be computationally intensive.

Because the cameras are modeled by projective transformations, lengths and angles are not invariant. Therefore, they cannot be used to solve the correspondence problem. The cross ratio or the ratio of the ratio of lengths is invariant, however. Other invariant properties include collinearity, coincidence, concurrency, tangency, and intersection. There are three constraints that are most important. These are 1) a uniqueness constraint, 2) the epipolar constraint, and the 3) ordering constraint. The uniqueness constraint provides that for a given point in one image, there is at most one matching point (the conjugate point) in the second image. The epipolar constraint provides that the conjugate point is constrained to be on the corresponding epipolar line. This is true in the ideal case in the absence of noise, but in real images, matching points may only be near the epipolar line. Finally, the ordering constraint provides that ordering is also preserved on epipolar lines when viewing a continuous, opaque surface. Utilizing these three constraints, the conjugate points for the corners and centroid of each sensor may be determined as described below.

Figure 7:
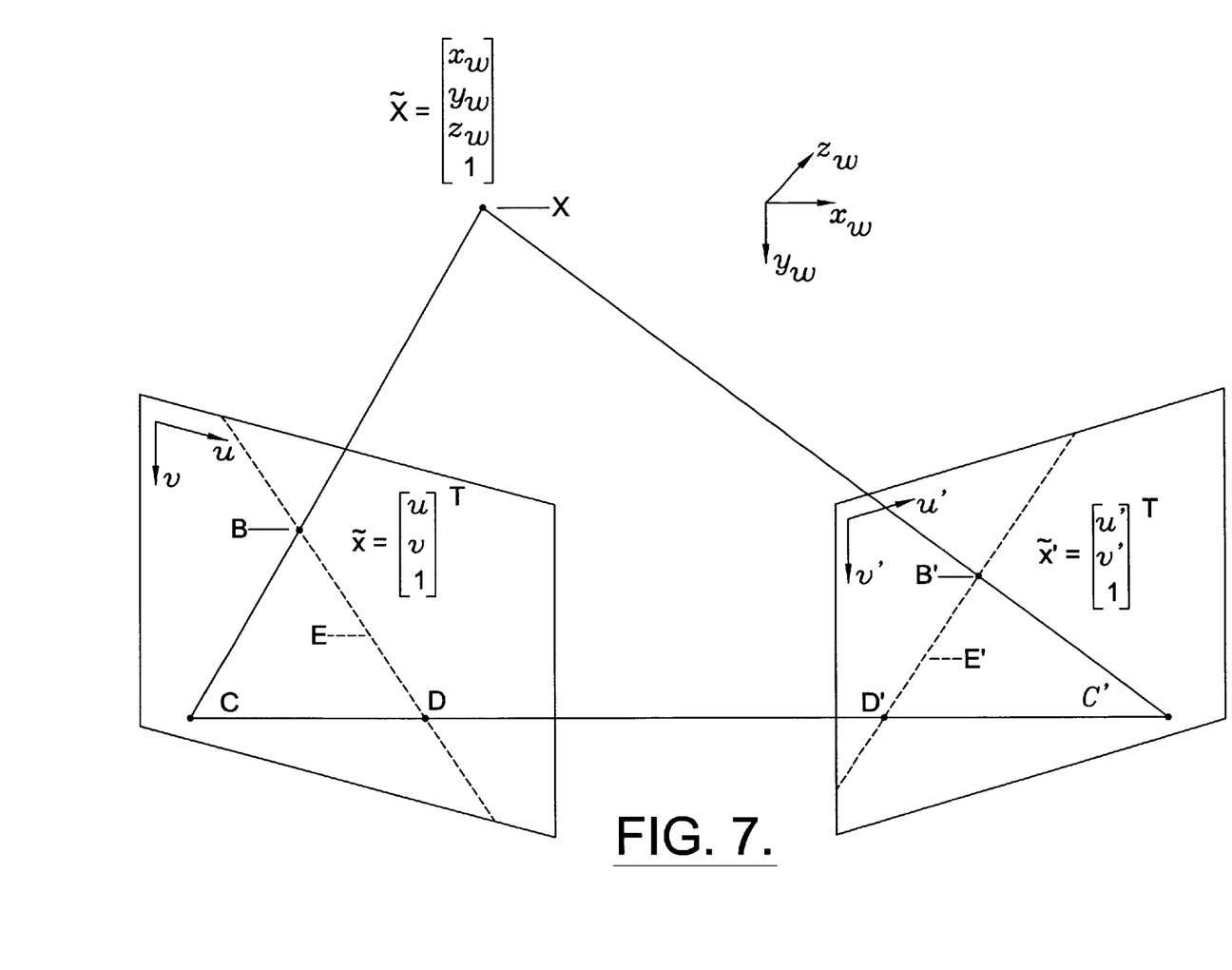
FIG. 7 illustrates one form of stereo camera geometry.

The imaging geometry is illustrated in FIG. 7. A point in space, X, is imaged on two retinal planes. While in an actual camera, the retinal plane is behind the lens center, without loss of generality, the retinal plane can be placed in front of the lens center for analytical purposes. The camera centers or focal spots are C and C' for the left and right cameras, respectively. The three points, C, C', and X define what is known as the epipolar plane, and the intersections of this plane with the two retinal planes are called epipolar lines. These are illustrated as the broken lines E and E' in FIG. 7 in the left and right images. The epipoles are the image of the other camera's center point. For example, D is the image of C' in the left camera and D' is the image of C in the right camera as illustrated in FIG. 7.

Knowledge of the epipolar geometry and the pixel coordinates of a point in one camera are sufficient to constrain the set of possible matching pixel coordinates in the second camera. This reduces the dimensionality of the search for matching points to a line search. The ordering and uniqueness constraints are then used to complete the matching. The corresponding image coordinates are constrained to be on the epipolar line in the ideal case. This is known as the epipolar constraint. As described in Haralick, Robert M., and Linda G. Shapiro. *Computer and Robot Vision, Volume II*. Reading, Mass.: Addison-Wesley Publishing Company, 1993, the epipolar constraint is fundamental and may be exploited to solve matching problems.

For corresponding image points:

$$\tilde{x}^T F \tilde{x}' = 0$$

where F is the 3-by-3 fundamental matrix, and $\tilde{x}$ and $\tilde{x}'$ are homogeneous pixel coordinates in the left and right images, respectively. The fundamental matrix can be calculated using the projection matrices from the camera calibration procedures.

$$F = A^{-T}[t - RR'^{-1}t']_\times RR'^{-1}A'^{-1}$$

where t is the translation vector, R is the rotation matrix, and A is the internal parameter matrix for the left camera. Equivalent quantities for the right camera are primed. The notation $[x]_\times$ denotes the matrix formulation of the cross product, so that $[x]_\times y$ denotes the cross product of the vectors x and y. For example, $$[x_1 \quad x_2 \quad x_3]_\times = \begin{bmatrix} 0 & -x_3 & x_2 \\ x_3 & 0 & -x_1 \\ -x_2 & x_1 & 0 \end{bmatrix}$$

Figure 8:
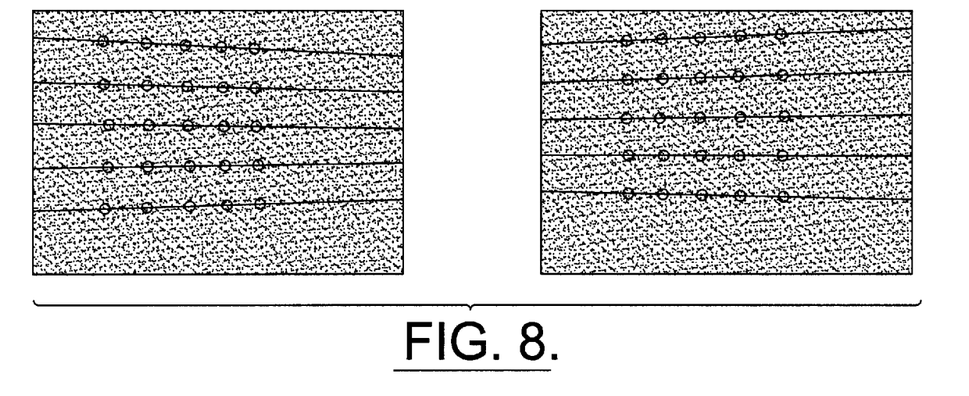
FIG. 8 is an illustration of a stereo image pair with epipolar lines illustrated.

FIG. 8 illustrates one potential problem using the epipolar lines. In each of the images, there are multiple epipolar lines passing through each point and each epipolar line passes through multiple points. Furthermore, because of imprecise optics, noise, image sampling, and numerical inaccuracies, the closest point to a particular epipolar line is not always the correct choice. Thus, an alternative method to selecting the point with its centroid closest to an epipolar line is preferred.

If F is the fundamental matrix and $\tilde{x}'$ is the pixel coordinate vector in the right image, then $I_{x'} = F\tilde{x}'$ is the equation of the epipolar line in the left image. This can then be used to compute the signed distance (d), up to an arbitrary scale factor, from a given point to the epipolar line. For any given epipolar line, this scale factor is constant and can, therefore, be neglected. If $\tilde{x}$ is the homogeneous pixel coordinate vector, then the signed distance d from the point $\tilde{x}$ to the line $I_{x'}$ is $d = \tilde{x}^T I_{x'}$.

Figure 9:
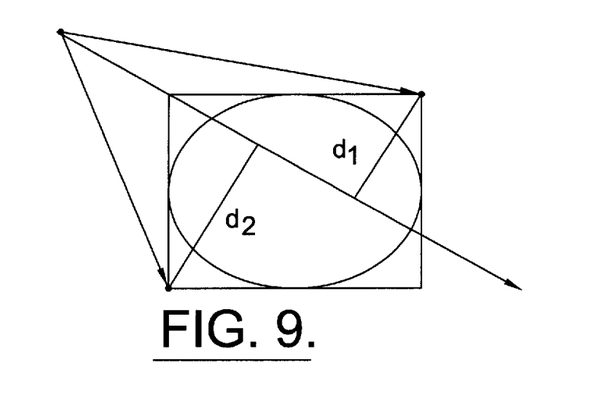
FIG. 9 is an illustration of a bounding box for an identified feature in an image with an epipolar line intersecting the bounding box.

FIG. 9 illustrates an epipolar line passing through a bounding box and is assumed to intersect the figure if the distances $d_1$ and $d_2$ have opposite signs (i.e. $\text{sgn}(d_1) = -\text{sgn}(d_2)$). A feature is then defined as "close" to an epipolar line if the epipolar line intersects the bounding box of the feature. To determine this intersection, the inner product of two diagonally opposite corners of the bounding box with the epipolar line is computed. If the epipolar line passes between the two points, the two inner products will have opposite signs. Any point that is close to the epipolar line, where close is defined as intersecting the bounding box, may be used in the ordering constraint to choose the proper match. The ordering constraint provides a way to choose the proper point when there are multiple intersections since it is preserved in a projective mapping, assuming opaque, continuous surfaces.

The pixel coordinates of the centroid and the bounding box of each sensor in each image are determined as described above utilizing the connected object method. Furthermore, the camera position and field of view are also preferably selected so that the number of features, m, in each image are the same, and that the same m objects have been imaged in each image. Thus, the corresponding points in the images may then be determined by, for each point in the left image, compute the corresponding epipolar line using the pixel coordinates in the left image and the fundamental matrix. It is then determined which features, if any, the epipolar line intersects in the right image. Intersection with a right image feature is determined by computing the signed distance from the epipolar line to opposite corners of the feature's bounding box. If the signed distances to the opposite corners have opposite signs, the line intersects the image feature. The left image features are sorted from left-to-right. For each left image feature, the number of epipolar line-bounding box intersections, n, is counted, and the intersected feature number is recorded. If n=0, the epipolar line does not intersect any of the features in the second image, correspondence cannot be achieved, and an error is returned. In general, each epipolar line can, and most likely will, intersect more than one image feature. However, because of the epipolar line ordering constraint, the leftmost feature in the right image that intersects the epipolar line and has not been previously matched is the proper conjugate point. This point is marked as matched and the process continues with the next left image feature. Thus, each of the features in may be matched with its corresponding feature in the other image for use in the point reconstruction.

A unit normal to the plane $\underline{P}$, containing corners P1, P2, P3, and P4, is computed by taking the cross-product of the vectors u and v between opposite corners, P1 and P3, and P2 and P4 (see FIG. 6) wherein a cross-product vector N=v×u is defined (block 212). As is visually illustrated in FIG. 5, normalizing this cross product vector N gives the unit normal $\tilde{n}$ to the plane $\underline{P}$ of the sensor top. The sensor contact point S is then determined by projecting from the position of the sensor centroid C in plane $\underline{P}$ along the unit normal vector $\tilde{n}$ a distance equal to the sensor depth corresponding to the height h (block 214). Thus, the normal vector $\tilde{n}$ and the contact point S may be determined by:

$$\tilde{n} = \frac{v \times u}{\|v \times u\|}$$
$$S = h\tilde{n}$$

Each contact point for each sensor 30' in the sensors 30 may be determined as described above. Furthermore, additional offsets or other determination from the contact point projected through the centroid may also be determined as may be needed depending on the particular sensor configuration utilized. Similarly, the normal vector may also be translated to the corner points to project the corners to the plane of contact so as to form an outline of the perimeter of contact of a sensor.

Because the location of each of the contact points are determined in three dimensional space (world or object space), the relative positions of the contact points of the sensors may be determined knowing the location in world or object space of the contact point S of each of the sensors 30. Furthermore, because the contact points are preferably determined based exclusively on the image data, the sensors need not come into physical contact with any measuring devices which may cause their relative positions to shift or change during measurement. Accordingly, the present invention provides for the determination of the spatial relationship of the contact point of sensors in an array without disturbing the sensors. The relationship of the sensors may be determined using images taken each time the sensors are applied to a patient. Therefore, because the contact point of each sensor may be determined individually, the determination of the spatial relationship of the contact point of sensors in an array does not require a fixed relationship between the sensors. Also, by determining the centroid of the sensor in a plane corresponding to the upper surface of the sensor and then projecting normal to that plane to a depth of the sensor, the contact point may be determined even when the contact point of the sensor is obscured.

One calibration process which may be utilized for calibrating the cameras 44 and 48 will now be described with reference to FIGS. 7 and 8. As is described above, the present invention utilizes photogrammetry to determine the contact points of the sensors 30 based on visible information related to the sensors configuration. Thus, the present invention utilizes the stereo cameras of FIG. 2 and stereo imaging to determine the contact points S.

As seen in FIG. 7, the point X in the world or object coordinate system is identified by a four-dimensional coordinate vector, $[s_y y_w z_w 1]^T$, in projective coordinates. The projective transformation of this world point onto the retinal or sensor plane is $[u\ v\ 1]^T$, where u and v are the horizontal and vertical pixel coordinates, respectively. The lens center is C, and corresponding points in the right camera are primed. The points B, B' correspond to point X in the two images.

The world and camera coordinate systems are assumed to be right-handed, i.e., z=x×y, with positive rotations around an axis defined by counter-clockwise rotation about the axis while looking down the coordinate axis towards the origin. The x-axis is defined to be positive to the right; the y-axis is defined to be positive downwards, and the z-axis is positive in the viewing direction. Rotation angles around the respective x, y and z-axes are denoted ω, φ and κ. These angles are sometimes called tilt, pan, and swing, or pitch, yaw and roll.

TABLE 1

Rotation Angle Conventions

| Axis rotation | Direction of positive rotation |
|---|---|
| x (tilt) | y to z |
| y (pan) | z to x |
| z (swing) | x to y |

The imaging system can be modeled as a linear projective operator, P, that maps the projective space, $P^3$, onto the retinal or sensor plane, $P^2$. This mapping from object or world space to the retinal plane can be expressed as:

$$s\tilde{x}=P\tilde{X},$$

where P is a 3-by-4 projection matrix, $\tilde{x}=[u\ v\ 1]^T$ is a homogeneous pixel coordinate, $\tilde{X}=[x_w\ y_w\ z_w\ 1]^T$ the homogeneous object coordinate vector and S is an arbitrary scale factor. See FIG. 6. If radial and tangential lens distortion are assumed to be negligible, the projection matrix is a function of 10 parameters.

$$P = P(t_x, t_y, t_z, \omega, \phi, \kappa, \alpha_u, \alpha_v, u_0, v_0)$$

To determine the 10 camera parameters, the sum of squared distances, d, between the observed points $[u\ v]^T$ and the projected points $[\hat{u}\ \hat{v}]^T$ is minimized.

$$d(t_x, t_y, t_z, \omega, \phi, \kappa, \alpha_u, \alpha_v, u_0, v_0) = \sum_{i=1}^{N}\left(\begin{bmatrix}\hat{u}_i\\\hat{v}_i\end{bmatrix} - \begin{bmatrix}u_i\\v_i\end{bmatrix}\right)^2$$

Since there are 10 unknown parameters, and two equations can be written for each object point (one each for the u and v pixel coordinates), a minimum of five target points is required. Determination of the parameters is a non-linear least-squares minimization problem.

These parameters include both external and internal camera parameters. External calibration parameters specify the camera position and orientation or pose using six parameters. These include a translation vector (t) from the camera to object coordinate system $[t_x\ t_y\ t_z]^T$, and the rotation angles $\omega$, $\phi$, and $\kappa$, which are the rotation angles around the x, y and z axes, respectively, around the coordinate axes. Interior calibration parameters specify the focal length, f, the pixel coordinates of the image center, $[u_0\ v_0]^T$, and the horizontal and vertical scale factors $k_u$ and $k_v$. The focal length and scale factors are combined to form the variables $\alpha_u$ and $\alpha_v$ where $\alpha_u = f k_u$ and $\alpha_v = f k_v$. Tangential and radial lens distortion may also be quantified.

Therefore, given a set of known coordinates in object space ("ground truth") and a corresponding set of pixel coordinates on the retinal plane, camera calibration is the process of determining the 10 parameters of the projection matrix that minimize the squared error between the observed points and the projection of the object points using the camera model, e.g., a pinhole camera.

The camera can be modeled as a pinhole camera where the relationship between the world coordinates of a point, $\tilde{X}$, and its projection onto the image plane with camera coordinates, $\tilde{x}$, are expressed mathematically as:

$$s\tilde{x} = P\tilde{X}$$

where $P = A[R|t]$ is the 3-by-4 projection matrix and s is an arbitrary scale factor. $R = R(\omega, \phi, \kappa)$ is a 3-by-3 rotation matrix that is a function of the camera viewing direction or camera pose, t is a 3-by-1 translation vector, and A is a 3-by-3 matrix of internal calibration parameters. These internal parameters include the focal length, scale factors, and the pixel coordinates principle point. Together, R and t describe the location and pose of the world coordinate system with respect to the camera. The matrix A transforms points from the camera's coordinate system into pixel coordinates on the image sensor.

The rotation matrix $R(\omega, \phi, \kappa)$, is the product of the rotation matrices for each individual axis. Multiplication by R rotates the world coordinate system into alignment with the camera coordinate system.

$$R(\omega, \phi, \kappa) = R(\kappa)R(\phi)R(\omega) =$$

$$\begin{bmatrix} \cos\phi\cos\kappa & \sin\omega\sin\phi\cos\kappa + \cos\omega\sin\kappa & -\cos\omega\sin\phi\cos\kappa + \sin\omega\sin\kappa \\ -\cos\phi\sin\kappa & -\sin\omega\sin\phi\sin\kappa + \cos\omega\cos\kappa & \cos\omega\sin\phi\sin\kappa + \sin\omega\cos\kappa \\ \sin\phi & -\sin\omega\cos\phi & \cos\omega\cos\phi \end{bmatrix}$$

where, $$R(\omega) = \begin{bmatrix} 1 & 0 & 0 \\ 0 & \cos\omega & \sin\omega \\ 0 & -\sin\omega & \cos\omega \end{bmatrix}$$

$$R(\phi) = \begin{bmatrix} \cos\phi & 0 & -\sin\phi \\ 0 & 1 & 0 \\ \sin\phi & 0 & \cos\phi \end{bmatrix}$$

$$R(\kappa) = \begin{bmatrix} \cos\kappa & \sin\kappa & 0 \\ -\sin\kappa & \cos\kappa & 0 \\ 0 & 0 & 1 \end{bmatrix}$$

The internal camera parameters are contained in the matrix A. These include the focal length, f, scale factors in the u and v directions, $k_u$ and $k_v$, and the coordinates $[u_0\ v_0]^T$ of the principal point.

$$A = \begin{bmatrix} fk_u & 0 & u_o \\ 0 & fk_v & v_o \\ 0 & 0 & 1 \end{bmatrix} = \begin{bmatrix} \alpha_u & 0 & u_o \\ 0 & \alpha_v & v_o \\ 0 & 0 & 1 \end{bmatrix}$$

where $\alpha = fk$. Combining the internal parameters, the rotation matrix, and the translation vector allows the projection equation to be written as:

$$s\begin{bmatrix}\hat{u}\\\hat{v}\\1\end{bmatrix} = \begin{bmatrix} \alpha_u & 0 & u_o \\ 0 & \alpha_v & v_o \\ 0 & 0 & 1 \end{bmatrix}\begin{bmatrix} r_{11} & r_{12} & r_{13} & t_x \\ r_{21} & r_{22} & r_{23} & t_y \\ r_{31} & r_{32} & r_{33} & t_z \end{bmatrix}\begin{bmatrix}x\\y\\z\\1\end{bmatrix}$$

If p denotes the i'th row of the projection matrix, then using the mathematical model of the camera, the pixel coordinates of the object point on the image sensor are calculated as follows:

$$\begin{bmatrix}\hat{u}\\\hat{v}\end{bmatrix} = \begin{bmatrix} \dfrac{p_1 \tilde{X}}{p_3 \tilde{X}} \\ \dfrac{p_2 \tilde{X}}{p_3 \tilde{X}} \end{bmatrix}.$$

After the camera parameters and projection matrices have been computed for each camera, object-space ("object point") coordinates can be estimated using corresponding points from two or more images of the same scene as is described briefly above and in more detail below.

The point reconstruction problem can be stated as follows: given a corresponding set of pixel coordinates from each camera and the projection matrices for each camera, P and P', determine the world coordinates of the point. The projection of an object point into each camera is represented as $$s\begin{bmatrix}u\\v\\1\end{bmatrix} = P\begin{bmatrix}x\\y\\z\\1\end{bmatrix} \qquad s'\begin{bmatrix}u'\\v'\\1\end{bmatrix} = P'\begin{bmatrix}x\\y\\z\\1\end{bmatrix}.$$

This can be rewritten as $$s\begin{bmatrix}u\\v\\1\end{bmatrix}=\begin{bmatrix}p\tilde{X}\\p\tilde{X}\\p\tilde{X}\end{bmatrix}\quad s'\begin{bmatrix}u'\\v'\\1\end{bmatrix}=\begin{bmatrix}p'\tilde{X}\\p'\tilde{X}\\p'\tilde{X}\end{bmatrix},$$

where $p_i$ is the i'th row of the projection matrix. Solving for $s=p_3\tilde{X}$ and $s'=P'_3\tilde{X}$ allows the projection equations from both cameras to be combined.

$$A\tilde{X}=\begin{bmatrix}p_1-p_3u\\p_1-p_3v\\p_1-p_3u'\\p_1-p_3v'\end{bmatrix}\begin{bmatrix}x\\y\\z\\1\end{bmatrix}=0$$

Because the coordinates of the object point are only determined up to an arbitrary scale factor in $p^3$, the norm of $\tilde{X}$ can be arbitrarily set to 1. The solution to the point reconstruction problem can then be expressed as a constrained minimization problem.

$$A\tilde{X}=0 \text{ subject to } \|\tilde{X}\|=1.$$

The solution to this constrained minimization problem is the norm 1 eigenvector that corresponds to the smallest eigenvalue of $A^TA$ where A and $A^T$ are as defined. This solution vector can be used to initialize the following non-linear optimization, if additional accuracy is required.

$$f(\tilde{X})=\left(u-\frac{p_1\tilde{X}}{p_3\tilde{X}}\right)^2+\left(v-\frac{p_2\tilde{X}}{p_3\tilde{X}}\right)^2+\left(u'-\frac{p'_1\tilde{X}}{p'_3\tilde{X}}\right)^2+\left(v'-\frac{p'_2\tilde{X}}{p'_3\tilde{X}}\right)^2$$

A point reconstruction algorithm is also described in Xu, G. and Z. Y. Zhang, *Epipolar Geometry in Stereo, Motion and Object Recognition: A Unified Approach* (1996) Kluwer Boston, Mass.: Academic Publishers.

As used herein, the term contact point may refer to a point of contact between an acoustic sensor and a patient. However, as will be appreciated by those of skill in the art, the contact point of a sensor may also be a plane of contact or a shape in a plane of contact. Accordingly, the present invention should not be construed as limited to determining only a single point of contact. Furthermore, while the present invention is described as projecting through the centroid, as will be appreciated by those of skill in the art in light of the present invention, any arbitrary point of the sensor may be projected through so as to determine the relative relationship of the sensors in a sensory array.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A method of determining an obscured contact point based on a visible portion of an acoustic sensor of a medical device contacting a patient from at least a first image containing an upper surface of the acoustic sensor from a first viewpoint and a second image containing the upper surface of the acoustic sensor from a second viewpoint different from the first viewpoint, the method comprising the steps of:

locating the acoustic sensor in the first image and the second image;

determining the location of a point on the upper surface of the acoustic sensor based on the location of the acoustic sensor in the first image and the corresponding location of the acoustic sensor in the second image;

determining a plane of the upper surface of the acoustic sensor based on the acoustic sensor in the first image and the corresponding acoustic sensor in the second image; and projecting a predetermined depth through the located point on the upper surface of the acoustic sensor in a direction having a predefined relationship with the plane of the visible portion of the acoustic sensor so as to determine the contact point of the obscured portion of the acoustic sensor.

2. A method according to claim 1, wherein the step of determining the location of a point on the upper surface of the acoustic sensor comprises the step of determining the location of a centroid of a visible portion of the acoustic sensor based on the location of the acoustic sensor in the first image and the corresponding location of the acoustic sensor in the second image.

3. A method according to claim 2, wherein the steps of determining the centroid, and determining a plane comprise the steps of:

determining the centroid of the sensor in each of the first and the second image; and determining a location of the centroid in three dimensional space from the centroid of the upper surface of the sensor in the first image and the centroid of the upper surface of the sensor in the second image.

4. A method according claim 3, wherein the step of projecting comprises the steps of:

determining a direction of a cross product of lines which pass through corners of the visible portion of the acoustic sensor; and projecting the predetermined depth from the centroid of the upper surface of the sensor in the direction of the cross product.

5. A method according to claim 4, further comprising the steps of:

establishing calipers in a direction orthogonal to directions of detected edges of the visible portion of the acoustic sensor; and moving the calipers until the calipers touch the located acoustic sensors so as to determine the locations of the corners of the visible portion of the acoustic sensor.

6. A method according to claim 5, wherein the visible portion of the acoustic sensor is a quadrangle.

7. A method according to claim 1, further comprising the steps of:

determining the contact points of a plurality of acoustic sensors; and determining the relative spatial relationship between the plurality of acoustic sensors based on the determination of the contact points of the plurality of acoustic sensors.

8. A method according to claim 1, wherein the acoustic sensor is substantially rectangular in shape such that the visible portion of the upper surface of the acoustic sensor is a quadrangle.

9. A method according to claim 1, wherein the first image is acquired by a first camera and wherein the second image is acquired by a second camera, the method further comprising the step of calibrating the first camera and the second camera so as to determine the relationship between the first viewpoint and the second viewpoint.

10. A method according to claim 9, wherein the step of calibrating comprises the steps of:
   acquiring at the first camera a first reference image containing a predefined configuration of landmarks;
   acquiring at the second camera a second reference image containing the predefined configuration of landmarks; and
   determining the spatial relationship between an image plane of the first camera and an image plane of the second camera based on the first and second reference images.

11. A method according to claim 9, wherein the step of calibrating comprises the steps of:
   computing camera parameters for each of the first and second cameras;
   computing projection matrices for each of the first and second cameras; and
   estimating object-space coordinates for each camera using corresponding points from at least two images of the same scene;
   wherein calibration of the cameras is indicated by coincidence of the object space coordinates for the corresponding points.

12. A method according to claim 1, wherein the locating step comprises the steps of:
   locating sensor positions in the first image;
   locating sensor positions in the second image; and
   determining a correspondence between the sensor positions in the first image and the sensor positions in the second image so that a sensor position in the first image is associated with the corresponding sensor position the second image.

13. A method according to claim 12, where the step of determining a correspondence comprises the steps of:
   determining an epipolar line for a sensor position in the first image;
   determining which of the sensor positions in the second image the epipolar line intersects; and
   associating a sensor position in the second image which the epipolar line intersects with the sensor position in the first image.

14. A method according to claim 13, wherein the step of associating comprises the steps of:
   determining if a plurality of sensor positions in the second image intersect the epipolar line; and
   associating sensor positions in the first image with sensor positions in the second image which intersect the epipolar line in an order in which the sensor positions in the first image intersect the epipolar line.

15. A method according to claim 13, wherein the step of determining which of the sensor positions in the second image the epipolar line intersects comprises the steps of:
   determining if the epipolar line intersects a bounding box around a sensor position;
   determining the signed distance between the epipolar line and opposite corners of the bounding box; and
   determining that the epipolar line intersects the sensor position if the signed distances between the epipolar line and the opposite corners of the bounding box are of opposite signs.

16. A system for determining an obscured contact point based on a visible portion of an acoustic sensor of a medical device contacting a patient from at least a first image containing an upper surface of the acoustic sensor from a first viewpoint and a second image containing the upper surface of the acoustic sensor from a second viewpoint different from the first viewpoint, comprising:
   means for locating the acoustic sensor in the first image and the second image;
   means for determining the location of a point on the upper surface of the acoustic sensor based on the location of the acoustic sensor in the first image and the corresponding location of the acoustic sensor in the second image;
   means for determining a plane of the upper surface of the acoustic sensor based on the acoustic sensor in the first image and the corresponding acoustic sensor in the second image; and
   means for projecting a predetermined depth through the located point on the upper surface of the acoustic sensor in a direction having a predefined relationship with the plane of the visible portion of the acoustic sensor so as to determine the contact point of the obscured portion of the acoustic sensor.

17. A system according to claim 16, wherein the means for determining the location of a point on the upper surface of the acoustic sensor comprises means for determining the location of a centroid of a visible portion of the acoustic sensor based on the location of the acoustic sensor in the first image and the corresponding location of the acoustic sensor in the second image.

18. A system according to claim 17, wherein the means for determining the location of a centroid, and the means for determining a plane comprise:
   means for determining the centroid of the sensor in each of the first and the second image; and
   means for determining a location of the centroid in three dimensional space from the centroid of the upper surface of the sensor in the first image and the centroid of the upper surface of the sensor in the second image.

19. A system according claim 18, wherein the means for projecting comprises:
   means for determining a direction of a cross product of lines which pass through corners of the visible portion of the acoustic sensor; and
   means for projecting the predetermined depth from the centroid of the upper surface of the sensor in the direction of the cross product.

20. A system according to claim 19, further comprising:
   means for establishing calipers in a direction orthogonal to directions of detected edges of the visible portion of the acoustic sensor; and
   means for moving the calipers until the calipers touch the located acoustic sensors so as to determine the locations of the corners of the visible portion of the acoustic sensor.

21. A system according to claim 20, wherein the visible portion of the acoustic sensor is a quadrangle.

22. A system according to claim 16, further comprising:
   means for determining the contact points of a plurality of acoustic sensors;
   means for determining the relative spatial relationship between the plurality of acoustic sensors based on the determination of the contact points of the plurality of acoustic sensors.

23. A system according to claim 16, wherein the acoustic sensor is substantially rectangular in shape such that the visible portion of the upper surface of the acoustic sensor is a quadrangle.

24. A system according to claim 16, wherein the first image is acquired by a first camera and wherein the second image is acquired by a second camera, the system further comprising means for calibrating the first camera and the second camera so as to determine the relationship between the first viewpoint and the second viewpoint.

25. A system according to claim 24, wherein the means for calibrating comprises:
   means for acquiring at the first camera a first reference image containing a predefined configuration of landmarks;
   means for acquiring at the second camera a second reference image containing the predefined configuration of landmarks; and
   means for determining the spatial relationship between an image plane of the first camera and an image plane of the second camera based on the first and second reference images.

26. A system according to claim 24, wherein the means for calibrating comprises:
   means for computing camera parameters for each of the first and second cameras;
   means for computing projection matrices for each of the first and second cameras; and
   means for estimating object-space coordinates for each camera using corresponding points from at least two images of the same scene;
   wherein calibration of the cameras is indicated by coincidence of the object space coordinates for the corresponding points.

27. A system according to claim 16, wherein the means for locating comprises:
   means for locating sensor positions in the first image;
   means for locating sensor positions in the second image; and
   means for determining a correspondence between the sensor positions in the first image and the sensor positions in the second image so that a sensor position in the first image is associated with the corresponding sensor position the second image.

28. A system according to claim 27, where the means for determining a correspondence comprises:
   means for determining an epipolar line for a sensor position in the first image;
   means for determining which of the sensor positions in the second image the epipolar line intersects; and
   means for associating a sensor position in the second image which the epipolar line intersects with the sensor position in the first image.

29. A system according to claim 28, wherein the means for associating comprises:
   means for determining if a plurality of sensor positions in the second image intersect the epipolar line; and
   means for associating sensor positions in the first image with sensor positions in the second image which intersect the epipolar line in an order in which the sensor positions in the first image intersect the epipolar line.

30. A system according to claim 28, wherein the means for determining which of the sensor positions in the second image the epipolar line intersects comprises:
   means for determining if the epipolar line intersects a bounding box around a sensor position;
   means for determining the signed distance between the epipolar line and opposite corners of the bounding box; and
   means for determining that the epipolar line intersects the sensor position if the signed distances between the epipolar line and the opposite corners of the bounding box are of opposite signs.

31. A computer program product for determining an obscured contact point based on a visible portion of an acoustic sensor of a medical device contacting a patient from at least a first image containing an upper surface of the acoustic sensor from a first viewpoint and a second image containing the upper surface of the acoustic sensor from a second viewpoint different from the first viewpoint, comprising:
   a computer readable storage medium having computer readable program code means embodied in said medium, said computer readable program code means comprising:
   computer readable program code means for locating the acoustic sensor in the first image and the second image;
   computer readable program code means for determining the location of a point on the upper surface of the acoustic sensor based on the location of the acoustic sensor in the first image and the corresponding location of the acoustic sensor in the second image;
   computer readable program code means for determining a plane of the upper surface of the acoustic sensor based on the acoustic sensor in the first image and the corresponding acoustic sensor in the second image; and
   computer readable program code means for projecting a predetermined depth through the located point on the upper surface of the acoustic sensor in a direction having a predefined relationship with the plane of the visible portion of the acoustic sensor so as to determine the contact point of the obscured portion of the acoustic sensor.

32. A computer program product according to claim 31, wherein the computer readable program code means for determining the location of a point on the upper surface of the acoustic sensor comprises computer readable program code means for determining the location of a centroid of a visible portion of the acoustic sensor based on the location of the acoustic sensor in the first image and the corresponding location of the acoustic sensor in the second image.

33. A computer program product according to claim 32, wherein the computer readable program code means for determining the location of a centroid, and the computer readable program code means for determining a plane comprise:
   computer readable program code means for determining the centroid of the sensor in each of the first and the second image; and
   computer readable program code means for determining a location of the centroid in three dimensional space from the centroid of the upper surface of the sensor in the first image and the centroid of the upper surface of the sensor in the second image.

34. A computer program product according to claim 33, wherein the computer readable program code means for projecting comprises:
   computer readable program code means for determining a direction of a cross product of lines which pass through corners of the visible portion of the acoustic sensor; and
   computer readable program code means for projecting the predetermined depth from the centroid of the upper surface of the sensor in the direction of the cross product.

35. A computer program product according to claim 34, further comprising:

computer readable program code means for establishing calipers in a direction orthogonal to directions of detected edges of the visible portion of the acoustic sensor; and computer readable program code means for moving the calipers until the calipers touch the located acoustic sensors so as to determine the locations of the corners of the visible portion of the acoustic sensor.

36. A computer program product according to claim 35, wherein the visible portion of the acoustic sensor is a quadrangle.

37. A computer program product according to claim 31, further comprising:

computer readable program code means for determining the contact points of a plurality of acoustic sensors;

computer readable program code means for determining the relative spatial relationship between the plurality of acoustic sensors based on the determination of the contact points of the plurality of acoustic sensors.

38. A computer program product according to claim 31, wherein the acoustic sensor is substantially rectangular in shape such that the visible portion of the upper surface of the acoustic sensor is a quadrangle.

39. A computer program product according to claim 31, wherein the first image is acquired by a first camera and wherein the second image is acquired by a second camera, the computer program product further comprising computer readable program code means for calibrating the first camera and the second camera so as to determine the relationship between the first viewpoint and the second viewpoint.

40. A computer program product according to claim 39, wherein the computer readable program code means for calibrating comprises:

computer readable program code means for acquiring at the first camera a first reference image containing a predefined configuration of landmarks;

computer readable program code means for acquiring at the second camera a second reference image containing the predefined configuration of landmarks; and computer readable program code means for determining the spatial relationship between an image plane of the first camera and an image plane of the second camera based on the first and second reference images.

41. A computer program product according to claim 39, wherein the computer readable program code means for calibrating comprises:

computer readable program code means for computing camera parameters for each of the first and second cameras;

computer readable program code means for computing projection matrices for each of the first and second cameras; and computer readable program code means for estimating object-space coordinates for each camera using corresponding points from at least two images of the same scene;

wherein calibration of the cameras is indicated by coincidence of the object space coordinates for the corresponding points.

42. A computer program product according to claim 31, wherein the computer readable program code means for locating comprises:

computer readable program code means for locating sensor positions in the first image;

computer readable program code means for locating sensor positions in the second image; and computer readable program code means for determining a correspondence between the sensor positions in the first image and the sensor positions in the second image so that a sensor position in the first image is associated with the corresponding sensor position the second image.

43. A computer program product according to claim 42, where the computer readable program code means for determining a correspondence comprises:

computer readable program code means for determining an epipolar line for a sensor position in the first image;

computer readable program code means for determining which of the sensor positions in the second image the epipolar line intersects; and computer readable program code means for associating a sensor position in the second image which the epipolar line intersects with the sensor position in the first image.

44. A computer program product according to claim 43, wherein the computer readable program code means for associating comprises:

computer readable program code means for determining if a plurality of sensor positions in the second image intersect the epipolar line; and computer readable program code means for associating sensor positions in the first image with sensor positions in the second image which intersect the epipolar line in an order in which the sensor positions in the first image intersect the epipolar line.

45. A computer program product according to claim 43, wherein the computer readable program code means for determining which of the sensor positions in the second image the epipolar line intersects comprises:

computer readable program code means for determining if the epipolar line intersects a bounding box around a sensor position;

computer readable program code means for determining the signed distance between the epipolar line and opposite corners of the bounding box; and computer readable program code means for determining that the epipolar line intersects the sensor position if the signed distances between the epipolar line and the opposite corners of the bounding box are of opposite signs.

* * * * *